United States Patent
Schaefer et al.

(10) Patent No.: US 9,354,215 B2
(45) Date of Patent: May 31, 2016

(54) METAL TO CERAMIC SEAL

(71) Applicant: DELPHI TECHNOLOGIES, INC., Troy, MI (US)

(72) Inventors: Evan J D Schaefer, Rochester Hills, MI (US); Kaius K. Polikarpus, Grand Blanc, MI (US); Wayne M. Chadwick, Grand Blanc, MI (US); Mark S. Alexander, Swartz Creek, MI (US)

(73) Assignee: Delphi Technologies, Inc., Troy, MI (US)

( * ) Notice: Subject to any disclaimer, the term of this patent is extended or adjusted under 35 U.S.C. 154(b) by 270 days.

(21) Appl. No.: 13/975,863

(22) Filed: Aug. 26, 2013

(65) Prior Publication Data

US 2015/0052976 A1   Feb. 26, 2015

(51) Int. Cl.
*G01N 33/00* (2006.01)
*G01N 27/407* (2006.01)

(52) U.S. Cl.
CPC ........ *G01N 33/0027* (2013.01); *G01N 27/4078* (2013.01)

(58) Field of Classification Search
CPC .................................................. G01N 27/4077
USPC ........... 73/23.31, 23.32, 31.05; 204/424–428, 204/431, 432; 338/34; 422/98
See application file for complete search history.

(56) References Cited

U.S. PATENT DOCUMENTS

| | | | |
|---|---|---|---|
| 5,329,806 A | | 7/1994 | McClanahan et al. |
| 5,467,636 A | * | 11/1995 | Thompson et al. .......... 73/23.31 |
| 5,602,325 A | | 2/1997 | McClanahan et al. |
| 5,616,825 A | * | 4/1997 | Achey et al. ................. 73/23.31 |
| 5,739,414 A | | 4/1998 | Paulus et al. |
| 5,874,663 A | * | 2/1999 | Fukaya et al. ............... 73/23.32 |
| 5,886,248 A | * | 3/1999 | Paulus et al. ................. 73/23.31 |
| 6,349,025 B1 | * | 2/2002 | Fraley et al. .................. 361/302 |
| 2004/0257747 A1 | * | 12/2004 | Stevenson et al. ............ 361/302 |
| 2005/0224348 A1 | * | 10/2005 | Satou et al. .................... 204/424 |
| 2005/0241368 A1 | * | 11/2005 | Yamauchi et al. .......... 73/31.05 |
| 2008/0294220 A1 | * | 11/2008 | Stevenson et al. ............. 607/36 |
| 2010/0202096 A1 | * | 8/2010 | Iyer .............................. 361/302 |

* cited by examiner

*Primary Examiner* — Hezron E Williams
*Assistant Examiner* — Hoang Nguyen
(74) *Attorney, Agent, or Firm* — Thomas M. Twomey

(57) ABSTRACT

A gas sensor includes a sensing element formed on a ceramic substrate, an insulator surrounding at least a portion of the sensing element, and a metal shell surrounding at least a portion of the sensing element. The gas sensor further includes a cured ceramic adhesive structure bonded to the insulator and the sensing element, to the insulator and the metal shell, or to the sensing element and the metal shell. The ceramic adhesive structure is disposed so as to mitigate gas leakage through the gas sensor.

3 Claims, 6 Drawing Sheets

METAL TO CERAMIC SEAL

BACKGROUND OF THE INVENTION

Exhaust sensors include an air reference channel to provide fluid communication with a source of fresh air. The air reference channel must be isolated from the automotive exhaust gas being sensed to prevent detrimental effects on the output of such a sensor that would result from contamination of the air reference. Prior attempts to achieve a seal between the exhaust gas and the air reference have used a seal of compacted talc powder between a sensing element and a sensor housing. Other approaches to achieve a seal between the exhaust gas and the air reference have included a glass seal, examples of which are disclosed in U.S. Pat. Nos. 5,329,806, 5,467,636, 5,602,325, 5,616,825, 5,739,414, 5,886,248, the entire disclosure of each of which are hereby incorporated herein by reference. However, improvements are always sought in any art.

BRIEF SUMMARY OF THE INVENTION

In an embodiment of the invention, a gas sensor includes a sensing element formed on a ceramic substrate, an insulator surrounding at least a portion of the sensing element, and a metal shell surrounding at least a portion of the insulator. The gas sensor further includes a cured ceramic adhesive structure that is bonded to the insulator and the metal shell, to the insulator and the sensing element, and/or to the sensing element and the metal shell. The ceramic adhesive structure reduces gas leakage through the sensor that might otherwise allow the air reference of the sensor to be contaminated by exhaust gas.

In an exemplary embodiment, the ceramic adhesive structure includes a single layer of a ceramic adhesive. In another exemplary embodiment, the ceramic adhesive structure includes a plurality of ceramic adhesive layers, with each ceramic adhesive layer bonded to at least one other ceramic adhesive layer. In a further aspect of the invention, a ceramic adhesive layer has a coefficient of thermal expansion (CTE) that is close to the CTE of each material to which the ceramic layer is bonded.

BRIEF DESCRIPTION OF THE DRAWINGS

The above-mentioned and other features and advantages of this invention will become apparent and be better understood by reference to the following description of embodiments of the invention in conjunction with the accompanying drawings, in which:

FIG. 5b is an end view of the portion of the prior art exhaust sensor of FIG. 5a.

DETAILED DESCRIPTION OF THE INVENTION

Figure 5A:
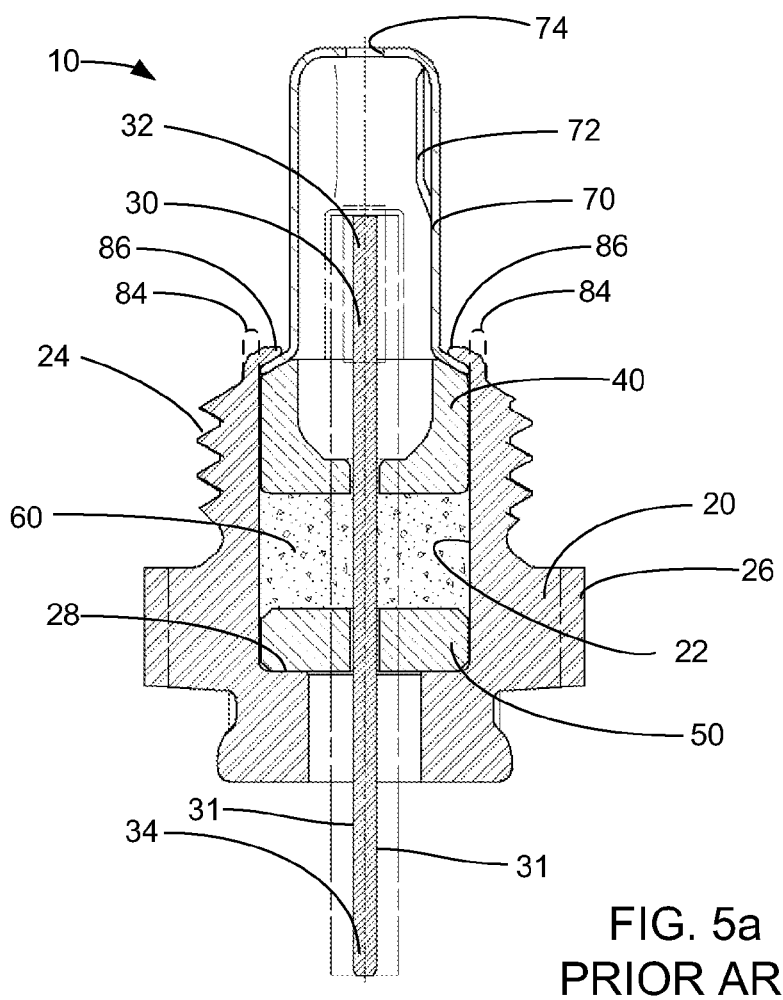
FIG. 5a is a cross sectional view of a portion of a prior art exhaust sensor.
Figure 5B:
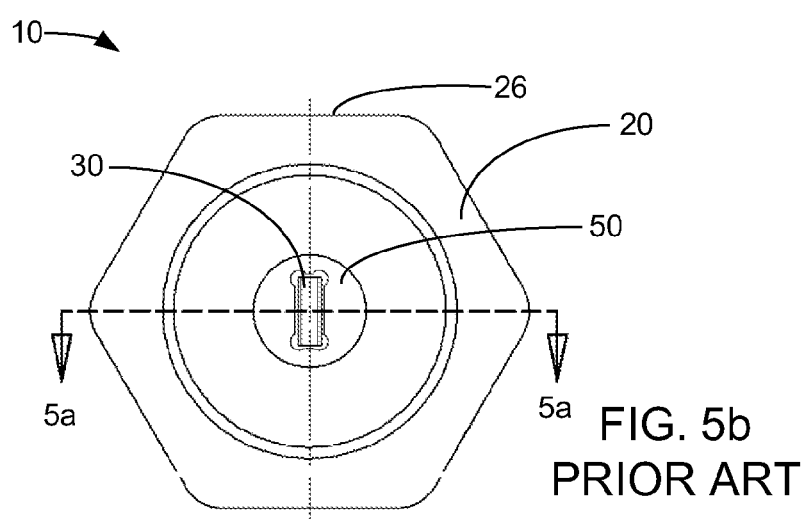

Referring to the drawings, wherein like reference numerals refer to like parts in several views, FIG. 5a shows a cross section of a sensor subassembly 10 as used in a prior art sensor and FIG. 5b shows an end view of the sensor subassembly of FIG. 5a. Referring to FIGS. 5a and 5b, the sensor subassembly 10 includes a metal shell 20. The shell 20 has an inner wall 22 that defines a substantially cylindrical cavity within the shell 20, with a step 28 defined at one end of the cavity within the shell 20. The shell 20 shown in FIGS. 5a and 5b has a screw thread 24 and a hexagonal shape 26 both defined on its outer surface. The screw thread 24 is configured to cooperate with a complementary screw thread defined, for example, in the wall of an exhaust pipe to facilitate mounting the sensor containing the subassembly 10. The hexagonal shape 26 is configured to cooperate with a complementary tool to facilitate rotating the sensor containing the subassembly 10 to tighten and to loosen the sensor in the exhaust pipe.

With continued reference to FIGS. 5a and 5b, the sensor subassembly 10 further includes a sensing element 30 formed from a ceramic substrate. The sensing element 30 has ceramic outer surfaces 31 on each side, a first end 32 which is exposed to the gas being sensed, and a second end 34 which is fluidically isolated from the gas being sensed. In a typical exhaust sensor application, a channel (not shown) within the sensing element 30 is open to the atmosphere surrounding the second end 34 of the sensing element 30, and the gas surrounding the second end 34 of the sensing element is thereby ported to an active sensing area near the first end 32 of the sensing element 30 to provide a reference gas against which the gas being sensed can be compared. In order to not contaminate the reference gas with the gas being sensed, fluidic isolation is necessary between the first end 32 and the second end 34 of the sensing element 30.

The sensor subassembly 10 in FIGS. 5a and 5b also includes a first insulator 40 and a second insulator 50, preferably made of ceramic. Both the first insulator 40 and the second insulator 50 are located within the cavity in the shell 20, and both have a clearance fit within the cavity. The sensor subassembly 10 in FIG. 5a also includes compacted powdered talc 60 located within the cavity in the shell 20, with the talc 60 being axially positioned between the first insulator 40 and the second insulator 50. The sensing element 30 is held in position substantially centered radially within the shell 20 by passing through holes defined in the first insulator 40 and the second insulator 50 and by passing through the compacted powdered talc 60. A shield 70 having a plurality of louvers 72 and a hole 74 defined therein is placed so as to surround the first end 32 of the sensing element 30. The shield 70 protects the sensing element 30 from mechanical damage, while the louvers 72 and the hole 74 allow fluid communication between the gas being sensed and the first end 32 of the sensing element 30.

A preferred method for assembling the sensor subassembly 10 is to insert the second insulator 50, a talc preform, the sensing element 30, and the first insulator 40 into the cavity defined within the shell 20. The talc preform is a frangible structure comprising talc powder and a binder that holds the talc powder together with sufficient strength to facilitate handling during the assembly of the sensor subassembly 10. The shield 70 is placed in contact with the first insulator 40, and an axial compressive force is applied to the shield 70, first insulator 40, talc preform, and second insulator 50 as the open end of the shell 20 is circumferentially crimped, deforming the open end of the shell 20 from the initial position shown by the broken line 84 to the final position 86 shown in FIG. 5a. The compressive force applied to the components during the assembly process is sufficient to crush the frangible talc preform, allowing the talc powder 60 to partially flow into clearance openings between the shell 20 and the first insulator 40, between the sensing element 30 and the first insulator 40, between the shell 20 and the second insulator 50, and between the sensing element 30 and the second insulator 50.

Figure 6:
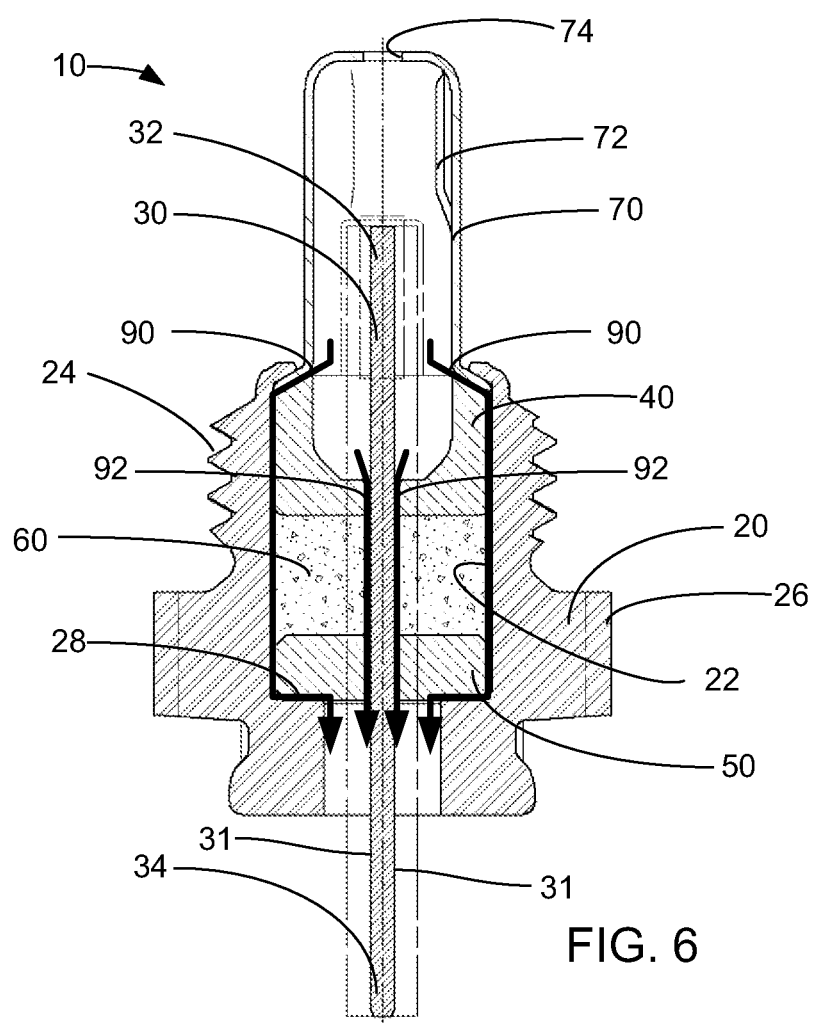
FIG. 6 is a representation of the prior art exhaust sensor of FIG. 5a indicating potential leak paths.

The tightly packed talc powder 60 acts to inhibit leakage of gas between the sensed gas at the first end 32 of the sensing element 30 and the atmosphere surrounding the second end 34 of the sensing element 30. However, the possibility exists for some non-zero level of leakage to be present. FIG. 6 depicts potential leak paths that may be present in a sensor subassembly 10 as described in relation to FIG. 5a and FIG. 5b. As depicted in FIG. 6, a first leak path 90 may be present, allowing leakage between the first insulator 40 and the shield 70, between the inner wall 22 of the shell 20 and the first insulator 40, between the inner wall 22 of the shell 20 and the talc 60, and between the inner wall 22 and step 28 of the shell 20 and the second insulator 50. A second leak path 92 may additionally or alternatively be present, allowing leakage between the sensing element 30 and the first insulator 40, the sensing element 30 and the talc 60, and the sensing element 30 and the second insulator 50. While not shown in FIG. 6, it will be appreciated that other leak paths incorporating segments of paths 90 and 92 depicted are possible. For example, a leak path may be present between the sensing element 30 and the first insulator 40, through the talc 60, and between the inner wall 22 and step 28 of the shell 20 and the second insulator 50. Another possible leak path may include the region between the shield 70 and the circumferential crimp in the shell 20.

The present invention includes added ceramic adhesive to the sensor structure of FIG. 5 described above in locations that are advantageous to mitigation of leak paths through the sensor. As used herein, the term ceramic adhesive is used to describe a ceramic matrix formed from a mixture of a mineral filler and an alkali silicate in water, wherein curing is achieved by a crystallization process. The mineral filler may comprise, by way of non-limiting examples, alumina, silica, aluminum nitride, magnesia, mica, silicon carbide, zirconia, and/or zirconium silicate. The composition of the ceramic adhesive can be selected to optimize its ability to bond to given materials (e.g. ceramics, metals, quartz) and/or to achieve a desired coefficient of thermal expansion of the cured ceramic adhesive. Ceramic adhesives that may be usable in the embodiments of the invention described herein include adhesives available from Aremco Products, Inc. under the Ceramabond™ name.

Figure 1:
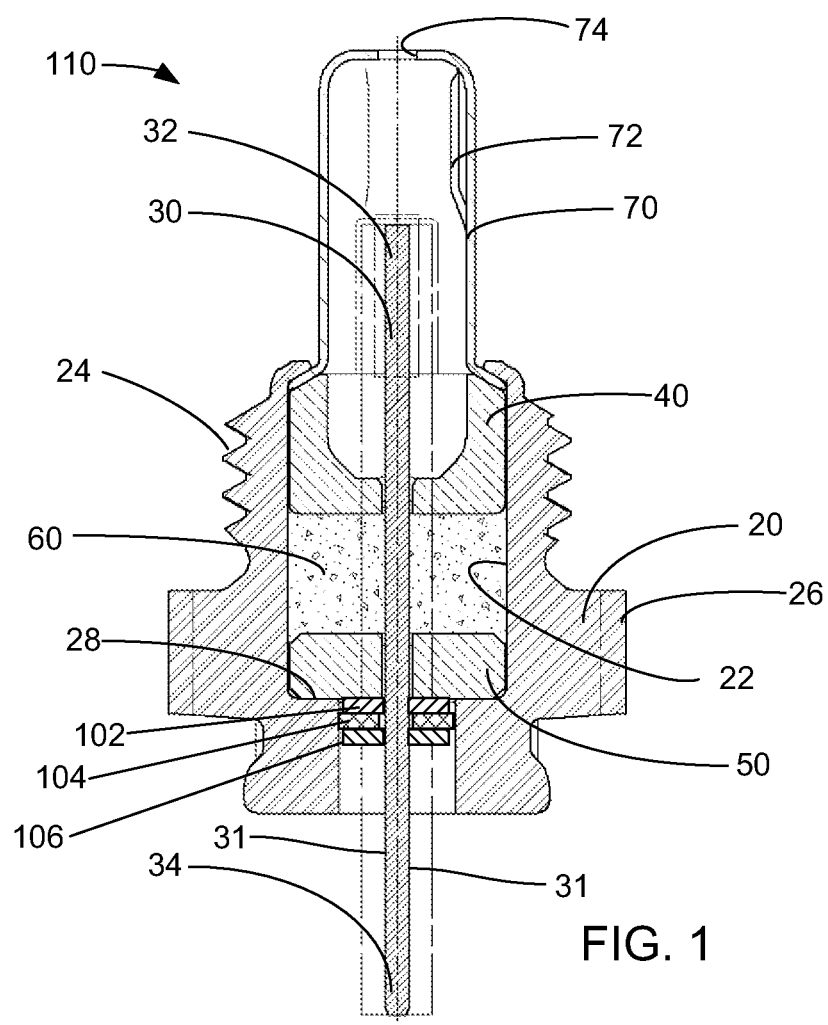
FIG. 1 is a representation of a first implementation of a portion of an exhaust sensor incorporating aspects of the present invention.

A first non-limiting example of a sensor that includes aspects of the present invention is shown in FIG. 1. The sensor subassembly 110 of FIG. 1 is similar to the sensor subassembly 10 depicted in FIG. 5, with the addition of ceramic adhesive layers 102, 104, and 106. Layers 102 and 106 preferably comprise a ceramic adhesive formulated to bond well to ceramics as well as to other ceramic adhesives, with a preferred coefficient of thermal expansion (CTE) after curing of approximately $7.5 \times 10^{-6}$ m/m/° C. Ceramic adhesive layer 102 is deposited as an annular layer contacting a face of second insulator 50 and the ceramic outer surfaces 31 of sensing element 30. Ceramic adhesive layer 104 preferably comprises a ceramic adhesive formulated to bond well to metal as well as to other ceramic adhesives, with a preferred CTE after curing of approximately $11.5 \times 10^{-6}$ m/m/° C. Layer 104 is deposited as an annular layer contacting shell 20 as well as a surface of layer 102. Layer 106 is deposited as an annular layer contacting the outer surfaces 31 of sensing element 30 as well as a surface of layer 104. After curing, the ceramic adhesive layers 102, 104, and 106 form a cured ceramic layer structure that is bonded to the sensing element 30, the second insulator 50, and the shell 20, thereby effectively sealing any leak paths that may have been present at the interfaces between the sensing element 30, the second insulator 50, and the shell 20.

Figure 2:
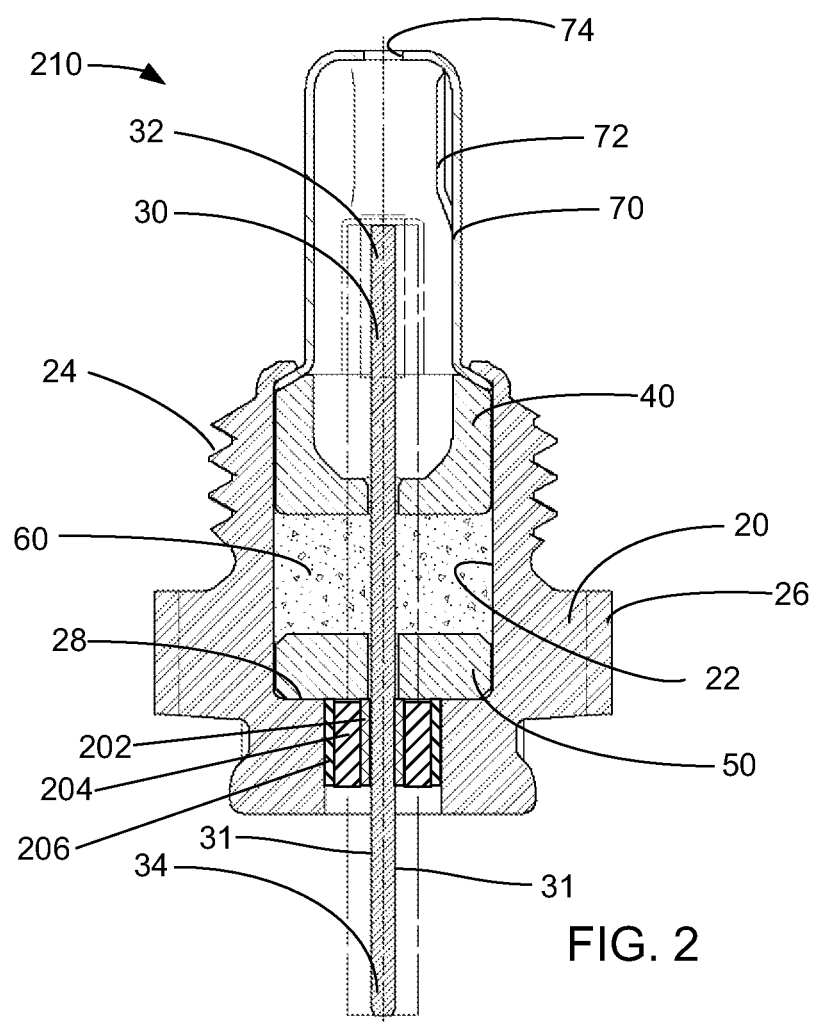
FIG. 2 is a representation of a second implementation of a portion of an exhaust sensor incorporating aspects of the present invention.

FIG. 2 depicts another non-limiting embodiment of a sensor that incorporates aspects of the present invention. The sensor subassembly 210 of FIG. 2 is similar to the sensor subassembly 10 depicted in FIG. 5, with the addition of ceramic adhesive layers 202, 204 and 206. Layer 206 preferably comprises a ceramic adhesive formulated to bond well to metal as well as to other ceramic adhesives, with a preferred CTE after curing of approximately $11.5 \times 10^{-6}$ m/m/° C. Layer 204 preferably comprises a ceramic adhesive formulated to bond well to other ceramic adhesives, with a preferred CTE after curing of approximately $13 \times 10^{-6}$ m/m/° C., so as to keep the entire ceramic adhesive structure 202, 204, 206 in compression by the shell 20 during heating and cooling of the sensor subassembly 210. In FIG. 2, layers 202, 204, and 206 are disposed so as to overlap at a given axial position, with layer 202 deposited in contact with the sensing element 30, layer 206 disposed in contact with the shell 20, and layer 204 disposed between layers 202 and 206 so as to contact both layer 202 and layer 206. After curing, the ceramic adhesive layers 202, 204, and 206 form a ceramic layer structure that is bonded to the sensing element 30 and the shell 20, thereby effectively sealing any leak paths that may have been present at the interfaces between the sensing element 30, the second insulator 50, and the shell 20. In the embodiment of FIG. 2, bonding between the ceramic adhesive structure 202, 204, 206 and the second insulator 50 is permitted but not required.

Figure 3:
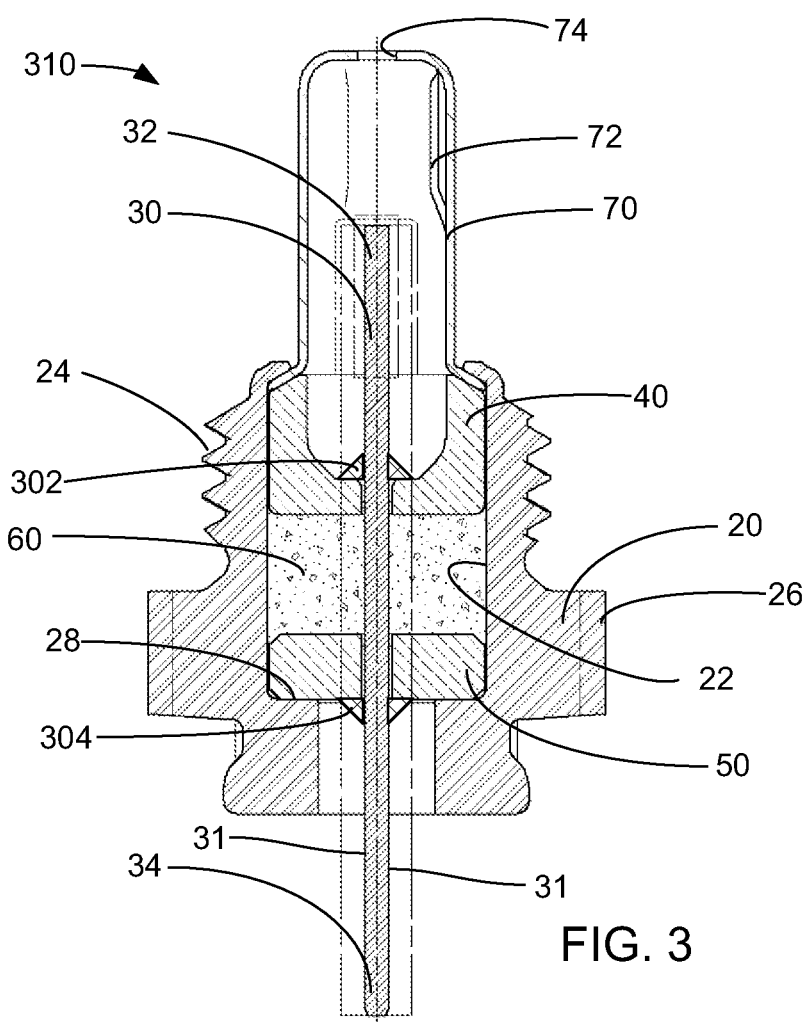
FIG. 3 is a representation of a third implementation of a portion of an exhaust sensor incorporating aspects of the present invention.

Another non-limiting embodiment of a sensor that incorporates aspects of the present invention is depicted in FIG. 3. The sensor subassembly 310 in FIG. 3 is similar to the sensor subassembly 10 depicted in FIG. 5, with the addition of ceramic adhesive structures 302 and 304. Structures 302 and 304 each comprises a ceramic adhesive formulated to bond well to ceramics as well as to other ceramic adhesives, with a preferred CTE after curing of approximately $7.5 \times 10^{-6}$ m/m/° C. As indicated in FIG. 3, ceramic adhesive structures 302 is disposed around the periphery of a section of the sensing element 30 so as to bond to both the sensing element 30 and to the first insulator 40. Ceramic adhesive structure 304 is disposed around the periphery of a section of the sensing element 30 so as to bond to both the sensing element 30 and to the second insulator 50. It will be appreciated that the embodiment of FIG. 3 is useful in mitigating leakage through a leak path that includes leakage between the sensing element 30 and one of the first insulator 40 and the second insulator 50, but does not address a leak path along the inner wall 22 of the shell 20.

Figure 4:
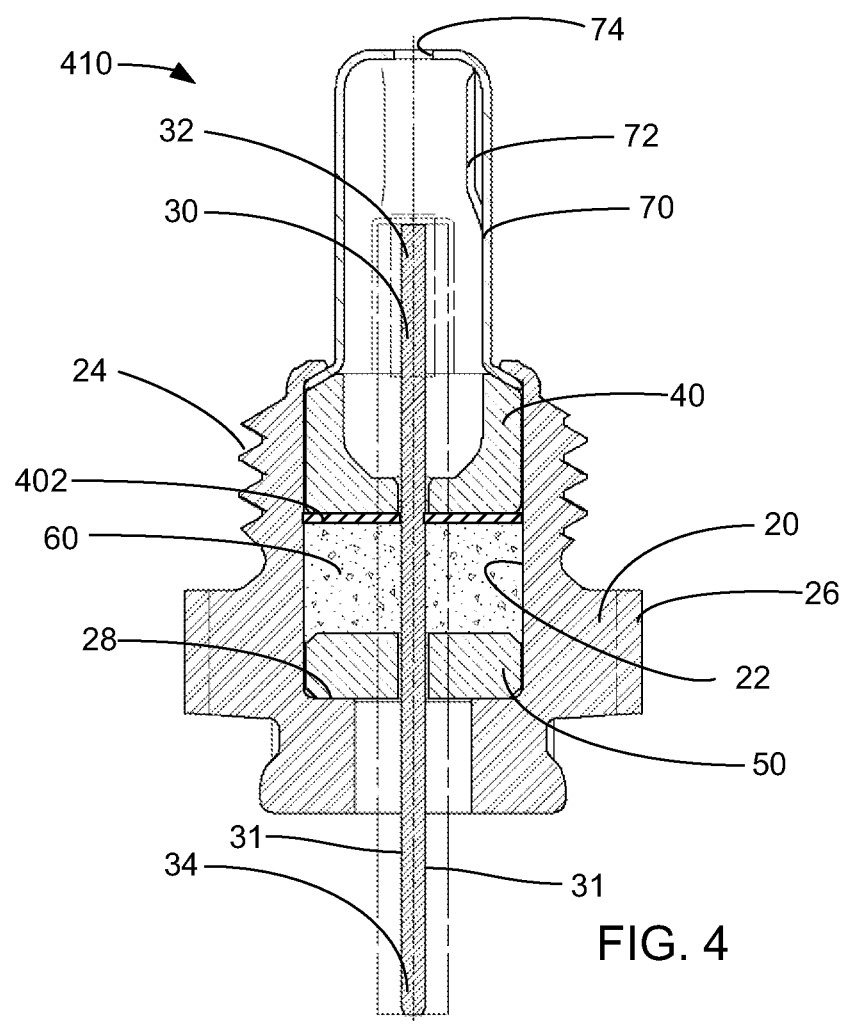
FIG. 4 is a representation of a fourth implementation of a portion of an exhaust sensor incorporating aspects of the present invention.

FIG. 4 depicts yet another non-limiting embodiment of a sensor that incorporates aspects of the present invention. The sensor subassembly 410 includes a layer 402 of ceramic adhesive disposed so as to bond to the inside wall 22 of the shell 20, a face of the first insulator 40, and the sensing element 30. Ceramic adhesive layer 402 comprises a ceramic adhesive formulated to bond to both ceramic and to metal, with a preferred CTE after curing of approximately $8.5 \times 10^{-6}$ m/m/° C.

Application of the uncured ceramic adhesive material to form the ceramic adhesive structures may be accomplished by brush, spray, or syringe. It will be appreciated that the embodiments depicted in FIG. 1 and in FIG. 2 allow application of the ceramic adhesive material to a conventionally produced sensor subassembly, such as subassembly 10 shown in FIG. 5. The embodiments depicted in FIG. 3 and in FIG. 4 require ceramic adhesive to be disposed to regions of a sensor subassembly that are not accessible in a completed subassembly, thus requiring modification to the manufacturing process to produce the subassembly.

In a representative sensor assembly, the shell 20 is made of a metal having a CTE of approximately $11.7 \times 10^{-6}$ m/m/° C., while the sensing element 30, the first insulator 40, and the second insulator 50 are made of ceramic materials having a CTE of approximately $7.6 \times 10^{-6}$ m/m/° C. It is desirable to select the ceramic adhesive materials to be used in the ceramic adhesive structure so that each ceramic adhesive material has a CTE after curing that is close to the CTE of the sensor component (i.e. metal or ceramic) to which the ceramic adhesive material is bonded. By using a plurality of ceramic adhesive materials in a ceramic adhesive structure, with appropriate dimensions for each of the plurality of ceramic adhesive materials in the ceramic adhesive structure, an effective coefficient of thermal expansion for the composite ceramic adhesive structure can be established allowing the entire assembly to be kept in compression by the shell during heating and cooling of the sensor.

While the invention has been described in terms of specific embodiments, the present invention can be further modified within the spirit and scope of this disclosure. This application is intended to cover any variations, uses, or adaptations of the present invention using the general principles disclosed herein. Further, this application is intended to cover such departures from the present disclosure as come within the known or customary practice in the art to which this invention pertains and which fall within the limits of the claims which follow.

The invention claimed is:

1. A gas sensor comprising:
   a sensing element formed on a ceramic substrate and having ceramic outer surfaces;
   an insulator surrounding at least a portion of the sensing element;
   a metal shell surrounding at least a portion of the insulator; and
   a cured ceramic adhesive structure bonded to the insulator and the sensing element, wherein the cured ceramic adhesive structure comprises a plurality of ceramic adhesive layers, and wherein each layer of the plurality of annular ceramic adhesive layers is bonded to at least one other layer of the plurality of ceramic adhesive layers and to the insulator and the metal shell, or to the ceramic outer surfaces of the sensing element and the metal shell.

2. The gas sensor of claim 1 wherein at least two adjoining ceramic adhesive layers have coefficients of thermal expansion that differ from each other.

3. The gas sensor of claim 1 wherein each of the plurality of ceramic adhesive layers has a coefficient of thermal expansion that differs by no more than $3.0 \times 10^{-6}$ m/m/° C. from the coefficient of thermal expansion of each adjoining ceramic adhesive layer to which it is bonded and by no more than $3.0 \times 10^{-6}$ m/m/° C. from the coefficient of thermal expansion of each of the sensing element, the insulator, and the metal shell to which the one of each ceramic adhesive layer is bonded.

* * * * *